US008770751B2

(12) United States Patent  (10) Patent No.: US 8,770,751 B2
Ferguson et al.  (45) Date of Patent: Jul. 8, 2014

(54) HYBRID SPECTRAL DOMAIN OPTICAL COHERENCE TOMOGRAPHY LINE SCANNING LASER OPHTHALMOSCOPE

(75) Inventors: R. Daniel Ferguson, Melrose, MA (US); Daniel X. Hammer, Bedford, NH (US); Nicusor V. Iftimia, Chelmsford, MA (US); Chad Bigelow, Cambridge, MA (US)

(73) Assignee: Physical Sciences, Inc., Andover, MA (US)

(*) Notice: Subject to any disclaimer, the term of this patent is extended or adjusted under 35 U.S.C. 154(b) by 253 days.

(21) Appl. No.: 13/237,419

(22) Filed: Sep. 20, 2011

(65) Prior Publication Data

US 2012/0062843 A1 Mar. 15, 2012

Related U.S. Application Data

(62) Division of application No. 12/964,518, filed on Dec. 9, 2010, now Pat. No. 8,033,665, which is a division of application No. 12/630,358, filed on Dec. 3, 2009, now Pat. No. 7,866,821, which is a division of application No. 11/799,315, filed on May 1, 2007, now Pat. No. 7,648,242.

(60) Provisional application No. 60/796,387, filed on May 1, 2006.

(51) Int. Cl.
  *A61B 3/10* (2006.01)
(52) U.S. Cl.
  USPC .......................................... 351/205; 351/210
(58) Field of Classification Search
  USPC .......................................... 351/210, 218, 221
  See application file for complete search history.

(56) References Cited

U.S. PATENT DOCUMENTS

| 4,264,152 A | 4/1981 | Crane |
| 4,443,075 A | 4/1984 | Crane |
| 4,561,436 A | 12/1985 | Munnerlyn |
| 4,569,354 A | 2/1986 | Shapiro et al. |
| 4,764,005 A | 8/1988 | Webb et al. |
| 4,765,730 A | 8/1988 | Webb |
| 4,768,873 A | 9/1988 | Webb |

(Continued)

FOREIGN PATENT DOCUMENTS

| EP | 0 307 185 | 3/1989 |
| EP | 0 770 370 | 5/1997 |

(Continued)

OTHER PUBLICATIONS

Alt et al., "Selective Targeting of the Retinal Pigment Epithelium Using an Acousto-Optic Laser Scanner," *Journal of Biomedical Optics*, vol. 10(6) (2005) pp. 064014-1-064014-11. (11 pgs.).

(Continued)

*Primary Examiner* — Jordan Schwartz
(74) *Attorney, Agent, or Firm* — Proskauer Rose LLP

(57) ABSTRACT

A method of imaging a retina of an eye includes combining an optical path of an optical coherence tomography (OCT) imager and an optical path of a line scanning laser ophthalmoscope (LSLO) imager using a system of optics. The method also includes using a single detector to switch between an OCT mode and a LSLO mode and acquiring images of the retina while switching between the OCT mode and the LSLO mode.

20 Claims, 6 Drawing Sheets

(56) References Cited

U.S. PATENT DOCUMENTS

| | | | |
|---|---|---|---|
| 4,768,874 | A | 9/1988 | Webb et al. |
| 4,781,453 | A | 11/1988 | Kobayashi |
| 4,856,891 | A | 8/1989 | Pflibsen et al. |
| 4,881,808 | A | 11/1989 | Bille et al. |
| 4,883,061 | A | 11/1989 | Zeimer |
| 4,886,351 | A | 12/1989 | Sabban et al. |
| 4,924,507 | A | 5/1990 | Chao et al. |
| 4,931,053 | A | 6/1990 | L'Esperance, Jr. |
| 4,964,717 | A | 10/1990 | Koester |
| 5,029,220 | A | 7/1991 | Juday |
| 5,094,523 | A | 3/1992 | Reznichenko et al. |
| 5,098,426 | A | 3/1992 | Sklar et al. |
| 5,106,184 | A | 4/1992 | Milbocker |
| 5,122,135 | A | 6/1992 | Dürr et al. |
| 5,129,400 | A | 7/1992 | Makino et al. |
| 5,243,368 | A | 9/1993 | Ito et al. |
| 5,252,999 | A | 10/1993 | Sukigara et al. |
| 5,309,187 | A | 5/1994 | Crossman et al. |
| 5,347,329 | A | 9/1994 | Ota |
| 5,353,073 | A | 10/1994 | Kobayashi |
| 5,360,010 | A | 11/1994 | Applegate |
| 5,360,424 | A | 11/1994 | Klopotek |
| 5,425,729 | A | 6/1995 | Ishida et al. |
| 5,430,509 | A | 7/1995 | Kobayashi |
| 5,437,274 | A | 8/1995 | Khoobehi et al. |
| 5,480,396 | A | 1/1996 | Simon et al. |
| 5,526,189 | A | 6/1996 | Heacock |
| 5,673,097 | A | 9/1997 | Heacock |
| 5,767,941 | A | 6/1998 | Ferguson |
| 5,777,719 | A | 7/1998 | Williams et al. |
| 5,778,016 | A | 7/1998 | Sucha et al. |
| 5,784,148 | A | 7/1998 | Heacock |
| 5,861,938 | A | 1/1999 | Heacock |
| 5,943,115 | A | 8/1999 | Ferguson |
| 5,949,520 | A | 9/1999 | Heacock |
| 5,976,502 | A | 11/1999 | Khoobehi et al. |
| 6,027,216 | A | 2/2000 | Guyton et al. |
| 6,099,127 | A | 8/2000 | Manivannan et al. |
| 6,186,628 | B1 | 2/2001 | Van de Velde |
| 6,199,986 | B1 | 3/2001 | Williams et al. |
| 6,267,477 | B1 | 7/2001 | Karpol et al. |
| 6,299,311 | B1 | 10/2001 | Williams et al. |
| 6,379,006 | B1 | 4/2002 | Eikelboom et al. |
| 6,471,691 | B1 | 10/2002 | Kobayashi et al. |
| 6,758,564 | B2 | 7/2004 | Ferguson |
| 6,890,076 | B2 | 5/2005 | Roorda |
| 7,118,216 | B2 | 10/2006 | Roorda |
| 7,284,859 | B2 | 10/2007 | Ferguson |
| 7,404,640 | B2 | 7/2008 | Ferguson et al. |
| 8,500,280 | B2 * | 8/2013 | Hirose ............... 351/206 |
| 2003/0231285 | A1 | 12/2003 | Ferguson |
| 2005/0012899 | A1 | 1/2005 | Ferguson |
| 2005/0254008 | A1 | 11/2005 | Ferguson et al. |
| 2006/0158655 | A1* | 7/2006 | Everett et al. ............. 356/479 |
| 2007/0216909 | A1* | 9/2007 | Everett et al. ............. 356/479 |
| 2008/0231808 | A1* | 9/2008 | Van de Velde ............ 351/221 |
| 2010/0315590 | A1* | 12/2010 | Ueno ................... 351/206 |

FOREIGN PATENT DOCUMENTS

| | | |
|---|---|---|
| JP | 11-253403 | 9/1999 |
| WO | WO 90/09141 | 8/1990 |
| WO | WO 93/08877 | 5/1993 |
| WO | WO 95/28989 | 11/1995 |
| WO | WO 97/40405 | 10/1997 |
| WO | WO 03/105679 | 12/2003 |

OTHER PUBLICATIONS

Hammer et al., "High Resolution Retinal Imaging With a Compact Adaptive Optics Spectral Domain Optical Coherence Tomography System," *Proceedings of SPIE*, vol. 6426 (2007) pp. 64261Q-1-64261Q-10. (10 pgs.).

Kobayashi et al., "Confocal Scanning Laser Ophthalmoscope With a Slit Aperture," *Measurement Science and Technology*, vol. 2 (1991) pp. 287-292. (6 pgs.).

Hammer et al., "Compact Scanning Laser Ophthalmoscope With High-Speed Retinal Tracker," *Applied Optics*, vol. 42, No. 22 (2003) pp. 4621-4632. (12 pgs.).

Heacock et al., "Imaging of the Choroid With the Scanning Slit Laser Ophthalmoscope (SSLO)," *The Society for Photo-Optical Instrumentation Engineers (SPIE)*, vol. 3591 (1999) pp. 456-464. (9 pgs.).

Hammer et al, "Precision Targeting With a Tracking Adaptive Optics Scanning Laser Ophthalmoscope," *Presented at SPIE BIOS 2006 Advanced Biomedical and Clinical and Diagnostic Systems IV* (San Jose, CA), (Jan. 21-26, 2006), [online], [retrieved on Jul. 31, 2007]. Retrieved from the Internet <URL: http://www.psicorp.com/publications/PDF/sr-1256.pdf> (11 pgs.).

Hammer et al., "Adaptive Optics Scanning Laser Ophthalmoscope for Stabilized Retinal Imaging," *Optics Express*, vol. 14, No. 8 (2006) pp. 3354-3367. (13 pgs.).

Bigelow et al., "Compact Multimodal Adaptive-Optics Spectral-Domain Optical Coherence Tomography Instrument for Retinal Imaging," *Journal of the Optical Society of America A*, vol. 24, No. 5 (May 2007) pp. 1327-1336. (10 pgs.).

Dreher et al., "Active Optical Depth Resolution Improvement of the Laser Tomographic Scanner" *Applied Optics*, vol. 28, No. 4 (1989) pp. 804-808. (5 pgs.).

Iftimia, et al. "Hybrid Retinal Imager Using Line-Scanning Laser Ophthalmoscopy and Spectral Domain Optical Coherence Tomography," *Optics Express*, vol. 14, No. 26 (2006) pp. 12909-12914. (12 pgs.).

Ferguson, et al "Tracking Adaptive Optics Scanning Laser Ophthalmoscope," *Proceedings of SPIE*, vol. 6138 (2006) pp. 613810-1-613810-9. (9 pgs.).

Hammer, et al. "Hybrid LSLO/SDOCT retinal imager," [online], [retrieved on Jul. 31, 2007]. Retrieved from the Internet <URL:http://www.psicorp.com/publications/PDF/sr-1287.pdf> (9 pgs.).

Department of Defense Handbook, "Laser Safety on Ranges and in Other Outdoor Areas," MIL-HDBK-828A, Appendix A: "Summary of Laser Safety Information for Fire Control Laser Systems.". (136 pgs.), 1996.

Johnson et al., "Laser Eye Injuries Among US Military Personnel," *Proceedings of SPIE*, vol. 4953 (2003) pp. 51-60. (10 pgs.).

Sasahara et al., "Optical Coherence Tomographic Observations Before and After Macular Hole Formation Secondary to Laser Injury," *American Journal of Ophthalmology*, vol. 136, No. 6 (2003) pp. 1167-1170. (4 pgs.).

Sakaguchi et al., "Amsler Grid Examination and Optical Coherence Tomography of a Macular Hole Caused by Accidental Nd:YAG Laser Injury," *American Journal of Ophthalmology*, vol. 130, No. 3 (2000) pp. 355-356. (2 pgs.).

Roach et al., "Retinal Response of *Macaca mulatta* to Picosecond Laser Pulses of Varying Energy and Spot Size," *Journal of Biomedical Optics*, in press. vol. 9, No. 6 (2004) pp. 1288-1296. (9 pgs.).

Webb, et al., "Confocal Scanning Laser Ophthalmoscope," *Applied Optics*, vol. 26, No. 8 (1987) pp. 1492-1499. (8 pgs.).

Ferguson et al., "A Line-Scanning Laser Ophthalmoscope (LSLO)," *Investigative Ophthalmology & Visual Science*, (2003). (2 pgs.).

Hammer et al., "Hand-Held Digital Line-Scanning Laser Ophthalmoscope (LSLO)," *Proceedings of SPIE*, vol. 5314 (2004) pp. 161-169. (9 pgs.).

Huang et al., "Optical Coherence Tomography," *Science*, vol. 254 (1991) pp. 1178-1181. (4 pgs.).

Cense et al., "In Vivo Depth-Resolved Birefringence Measurements of the Human Retinal Nerve Fiber Layer by Polarization-Sensitive Optical Coherence Tomography," *Optics Letters*, vol. 27, No. 18 (2002) pp. 1610-1612. (3 pgs.).

Park et al., "Real-Time Multi-Functional Optical Coherence Tomography," *Optics Express*, vol. 11, No. 7 (2003) pp. 782-793. (12 pgs.).

Fercher et al., "Measurement of Intraocular Distances by Backscattering Spectral Interferometry," *Optics Communications*, vol. 117 (1995) pp. 43-48. (6 pgs.).

Hausler et al., "'Coherence Radar' and 'Spectral Radar'—New Tools for Dermatological Diagnosis," *Journal of Biomedical Optics*, vol. 3, No. 1 (1998) pp. 21-31. (11 pgs.).

(56) References Cited

OTHER PUBLICATIONS

Fercher et al., Optical Coherence Tomography—Principles and Applications, *Institute of Physics Publishing Reports on Progress in Physics*, vol. 66 (2003) pp. 239-303. (65 pgs.).

"American National Standard for Safe Use of Lasers" *Laser Institute of America*, (2000). (185 pgs.).

Yun et al., "High-Speed Optical Frequency-Domain Imaging," *Optics Express*, vol. 11, No. 22 (2003) pp. 2953-2963. (9 pgs.).

Drexler W et al., "Enhanced Visualization of Macular Pathology With the Use of Ultrahigh-Resolution Optical Coherence Tomography," *Archives of Ophthalmology*, vol. 121 (2003) pp. 695-706. (12 pgs.).

Wojtkowski et al., "In Vivo Human Retinal Imaging by Fourier Domain Optical Coherence Tomography," *Journal of Biomedical Optics*, vol. 7, No. 3 (2002) pp. 457-463. (7 pgs.).

Wojtkowski et al., "Real-Time In Vivo Imaging by High-Speed Spectral Optical Coherence Tomography," *Optics Letters*, vol. 28, No. 19 (2003) pp. 1745-1747. (3 pgs).

Yun et al., "High-Speed Spectral-Domain Optical Coherence Tomography at 1.3 μm Wavelength," *Optics Express*, vol. 11, No. 26 (2003) pp. 3598-3604. (7 pgs.).

Leitgeb et al., "Performance of Fourier Domain vs. Time Domain Optical Coherence Tomography," *Optics Express*, vol. 11, No. 8 (2003) pp. 889-894 (6 pgs.).

de Boer et al., "Improved Signal-to Noise Ratio in Spectral-Domain Compared with Time-Domain Optical Coherence Tomography," *Optics Letters*, vol. 28, No. 21 (2003) pp. 2067-2069. (3 pgs.).

White et al., "In Vivo Dynamic Human Retinal Blood Flow Imaging Using Ultra-High-Speed Spectral Domain Optical Doppler Tomography," *Optics Express*, vol. 11, No. 25 (2003) pp. 3490-3497. (8 pgs.).

Nassif et al., "In Vivo High-Resolution Video-Rate Spectral-Domain Optical Coherence Tomography of the Human Retina and Optic Nerve," *Optics Express*, vol. 12, No. 3 (2004) pp. 367-376. (10 pgs.).

Hammer, et al., "Technological Advances Improve Retinal Diagnostics," *Biophotonics International*, vol. 10, No. 9 (2003) p. 20. (2 pgs.).

Hammer et al., "Image Stabilization for Scanning Laser Ophthalmoscopy," *Optics Express*, vol. 10, No. 26 (2002) pp. 1542-1549. (8 pgs.).

Hammer et al., "Tracking Scanning Laser Ophthalmoscope (TSLO)," *Proceedings of SPIE*, vol. 4951 (2003) pp. 208-217. (10 pgs.).

Hammer et al., "Active Retinal Tracker for Clinical Optical Coherence Tomography Systems," *Journal of Biomedical Optics*, in press. vol. 10(2) (2005) pp. 024038-1-024038-11. (11 pgs.).

Ferguson et al., "Tracking Optical Coherence Tomography," *Optics Letters*, vol. 29, No. 18 (2004) pp. 2139-2141. (3 pgs.).

Hammer et al., "Advanced Scanning Methods With Tracking Optical Coherence Tomography," *Optics Express*, vol. 13, No. 20 (2005) pp. 7937-7947. (11 pgs.).

Ferguson et al., "Wide-Field Retinal Hemodynamic Imaging With the Tracking Scanning Laser Ophthalmoscope," *Optics Express*, vol. 12, No. 21 (2004) pp. 5198-5208. (11 pgs.).

Ishikawa et al., "Retinal Nerve Fiber Layer Assessment Using Optical Coherence Tomography With Active Optic Nerve Head Tracking," *Investigative Ophthalmology & Visual Science*, vol. 47, No. 3 (2006) pp. 964-967. (4 pgs.).

Liang et al., "Supernormal Vision and High-Resolution Retinal Imaging Through Adaptive Optics," *Journal of the Optical Society of America A*, vol. 14, No. 11 (1997) pp. 2884-2892. (9 pgs.).

Roorda et al., "Adaptive Optics Scanning Laser Ophthalmoscopy," *Optics Express*, vol. 10, No. 9 (2002) pp. 405-412. (8 pgs.).

Hammer et al., "Line-Scanning Laser Ophthalmoscope," *Journal of Biomedical Optics*, vol. 11(4) (2006) pp. 041126-1-041126-10. (10 pgs.).

Thibos et al., "Standards for Reporting the Optical Aberrations of Eyes," *Journal of Refractive Surgery*, vol. 18 (2002) pp. S652-S660. (9 pgs.).

Curcio et al., "Packing Geometry of Human Cone Photoreceptors: Variation With Eccentricity and Evidence for Local Anisotropy," *Visual Neuroscience*, vol. 9 (1992) pp. 169-180. (12 pgs.).

Vogel et al., "Retinal Motion Estimation in Adaptive Optics Scanning Laser Ophthalmoscopy," *Optics Express*, vol. 14, No. 2 (2006) pp. 487-497. (11 pgs.).

International Search Report for International Application No. PCT/US2007/010553 dated Apr. 28, 2008 (3 pages).

A.Gh. Podoleanu and D.A. Jackson, "Combined Optical Coherence Tomograph and Scanning Laser Ophthalmoscope," *Electronics Letters*, vol. 34 No. 11 (May 28, 1998) (2 pgs.).

\* cited by examiner

HYBRID SPECTRAL DOMAIN OPTICAL COHERENCE TOMOGRAPHY LINE SCANNING LASER OPHTHALMOSCOPE

This application is a divisional of prior application Ser. No. 12/964,518, filed on Dec. 9, 2010, which is a divisional of application Ser. No. 12/630,358 filed on Dec. 3, 2009, now U.S. Pat. No. 7,866,821, which is a divisional of application Ser. No. 11/799,315 filed on May 1, 2007, now U.S. Pat. No. 7,648,242, which claims the benefit of and priority to U.S. Provisional Patent Application No. 60/796,387 filed May 1, 2006, all of which are owned by the assignee of the instant application and the disclosures of which are incorporated herein by reference in their entireties.

STATEMENT OF GOVERNMENT INTEREST

This invention was made with government support under Air Force Contract No. FA9550-05-C-0181. The government may have certain rights in the invention.

FIELD OF THE INVENTION

This invention relates generally to optical imaging, and more particularly, to a device that combines a line-scanning laser ophthalmoscope and a spectral domain optical coherence tomography system for retinal imaging.

BACKGROUND OF THE INVENTION

Fundus and retinal imaging are important diagnostics in ophthalmology. Advanced imaging technologies now exist to detect tissue changes that occur due to retinal injuries not discernable with fundus photography. For example, optical coherence tomography (OCT) can provide depth-resolved images of ocular tissues approaching cellular resolution. The confocal scanning laser ophthalmoscope (SLO) also plays an important role in high-contrast visualization of thermal and other damage near sensitive retinal anatomy (e.g., the fovea).

OCT is an emerging technology for micrometer-scale, cross-sectional imaging of biological tissue and materials. A major application of OCT is ophthalmic imaging of the human retina in vivo. The Spectral-Domain OCT (SDOCT) improvement of the traditional time domain OCT (TDOCT) technique, known also as Fourier domain OCT (FDOCT), makes this technology suitable for real-time cross-sectional retinal imaging at video rate. At high speed, the need for vertical realignment of "A-scan" depth profiles is effectively eliminated across single B-scans, revealing a truer representation of retinal topography and the optic nerve head. Although B-scan image distortion by involuntary eye movement is reduced, transverse eye motion remains an issue for 3-D imaging and individual scan registration. Stabilized 3D OCT imaging can provide an en face fundus views for locating any given B-scan relative to retinal landmarks. Alternatively, simultaneous or interleaved live fundus imaging can also provide good retinal coordinates for a given B-scan, subject to the limitations of inter-frame eye motion.

The fusion of wide-field, line scanning laser ophthalmoscope (LSLO) retinal imaging with SDOCT imaging can enhance the clinician's ability to quickly assess pathologies in linked, complementary views with a simple, compact instrument. To make the ocular interface of future SDOCT systems more efficient, cost-effective, compact, and eventually field portable, neither complex motion stabilization systems nor opto-mechanical integration of secondary fundus cameras are desirable. Yet without precise knowledge of the OCT scan coordinates within the live fundus image to guide scan acquisition and interpretation, the diagnostic utility of this powerful imaging modality is limited.

The model for most clinical imaging systems to date has been the large stationary, desk-sized platforms with slit-lamp style human interface, bulky enclosure, numerous secondary optical or physical adjustment features, tethered power conditioning and signal processing units, computer, mouse and keyboard, and CRT monitor. These units generally require the subjects to adapt their posture to the instruments, rather than vice-versa. They typically combine the user interface and image acquisition functions with the image processing functions, the image analysis functions and the patient database. What is needed is an imaging system that can adapt to the patient, one where the operator, technician or medic can gather data, and an eye injury expert can provide analysis remotely based on the data recorded.

SUMMARY OF THE INVENTION

The invention, in one embodiment, features a system to provide images of the retina of an eye using a single compact instrument. The retinal imaging system can be a combination of an OCT system (e.g., a SDOCT system) and a LSLO system. In some embodiments, the SDOCT and LSLO share the same imaging optics and line scan camera for both OCT and LSLO imaging modes. Co-registered high contrast wide-field en face retinal LSLO and SDOCT images can be obtained non-mydriatically with less than 600 microwatts of broadband illumination at 15 frames/sec. The LSLO/SDOCT hybrid instrument can have important applications in clinical ophthalmic diagnostics and emergency medicine. The fusion of the wide-field, LSLO retinal imaging with SDOCT imaging can enhance the clinician's ability to quickly assess pathologies in linked, complementary views with a simple, compact instrument. Knowledge of the OCT scan coordinates within the live fundus image to guide scan acquisition and interpretation can enhance the diagnostic utility of OCT. For example, non-mydriatic, live retinal imaging (no pupil dilation), which requires no more than a 3 mm pupil in the human eye, usually depends on the use of NIR illumination to inhibit the pupil closure reflex. This is the case for the broadband SLD illumination beam from 800 nm to 900 nm, which for most subjects is still visible at <1 mW, but not bright or aversive, and allows imaging through a natural 2 to 3 mm pupil under subdued lighting conditions. The integration of hand-held LSLO technology with SDOCT can use the 3 mm pupil of the eye in two ways. First, the central 1 mm portion of the pupil is used as the SLD beam entrance pupil for both subsystems, but the exit pupils are separated. The returning light of the SDOCT passes back though the same 1 mm pupil, to function as an interferometer. The LSLO system can use the 3 mm annular aperture surrounding the central pupil area as its exit pupil for imaging the scattered light from the retina, thereby also avoiding corneal reflections from the entrance pupil. Second, the left and right sub-apertures of the LSLO annular aperture can be imaged to left and right detector arrays in order to form an LSLO stereo pair. This may be useful for direct visual assessment of gross retinal features and damage such as retinal hemorrhage.

In one aspect, there is an apparatus that includes a housing and a system of optical components disposed in the housing. The optical components are capable of operating in a LSLO mode and an OCT mode. The optical components include a first source to provide a first beam of light for the OCT mode, a second source to provide a second beam of light for the LSLO mode, and a first optic. In the OCT mode, the first optic scans, using a first surface of the first optic, the first beam of light along a retina of an eye in a first dimension and descans using the first surface, a first light returning from the eye in the first dimension to a detection system. In the LSLO mode, the first optic passes the second beam of light to the retina of the eye through a second surface of the first optic.

In another aspect, there is an apparatus that includes a housing and a system of optical components disposed in the housing capable of operating in an LSLO mode and an OCT mode. The system of optical components includes a first optic. In the OCT mode, the first optic redirects, using a first surface of the optic, a beam of light from a first source to an object to be scanned. The first optic also uses the first surface to redirect light returning from the object scanned. A second surface of the first optic redirects light dispersed by a grating to a detection system. In the LSLO mode, the first optic passes light returning from the object scanned to the detection system.

In another aspect, there is a method for imaging a retina of an eye. The method includes acquiring an OCT image of the eye by receiving, on a one-dimensional detector, a first light returning from the eye. A first electrical signal responsive to the first light is provided at each of a plurality of locations along the one-dimensional detector. The first electrical signal is combined with a reference signal from a reference arm. The first electrical signal and the reference signal is associated with the OCT image of the eye. In the LSLO mode, the method includes acquiring a LSLO image of the eye by receiving, on the one-dimensional detector, a second light returning from the eye. A second electrical signal is provided which is responsive to the second light at each of a plurality of locations along the one-dimensional detector. The second electrical signal is indicative of the LSLO image of the eye. The method also includes interleaving acquisition of the OCT image of the eye and the LSLO image of the eye.

In yet another aspect, there is an optical apparatus including a line scanning laser ophthalmoscope (LSLO) mode and an optical coherence tomography (OCT) mode. The optical apparatus includes a first source of a beam of light suitable for use in the LSLO mode and a second source of a beam of light suitable for use in the OCT mode. A lens receives the beam of light from the first source and provides a line of light for use in the LSLO mode. The apparatus also includes an optic. In the OCT mode, the optic redirects a beam of light from the second source to an object to be scanned, using a first surface of the optic. The optic uses the first surface to redirect the light returning from the object scanned and uses the second surface of the optic to redirect light dispersed into an OCT line configuration by a grating to a detection system. In the LSLO mode, the optic passes light returning from the object scanned to the detection system. The optic apparatus also includes a scanner. In the LSLO mode, the scanner scans a first portion of an object with the line of light in a direction perpendicular to the line through at least one lens. The scanner also descans light returning from the object in a LSLO line configuration. In the OCT mode, the scanner scans a second portion of the object with the beam of light and redirects light returning from the object. The detection system includes a one-dimensional detector. In the LSLO mode, the detection system receives the light descanned from the object and provides an electrical signal responsive to the light descanned at each of a plurality of locations along the LSLO line configuration. The electrical signal is indicative of a LSLO image of the object. In the OCT mode, the detection system receives the light redirected from the mirror and provides an electrical signal responsive to the light redirected at each of a plurality of locations along the OCT line configuration. The detection system combines the electrical signal with a reference signal from a reference arm. The electrical signal and the reference signal is associated with an OCT image of the object.

In another aspect, there is a method of imaging a retina of an eye. The method includes combining an optical path of an OCT imager and an optical path of a LSLO imager using a system of optics. A single detector is used to switch between an OCT mode and a LSLO mode. The method also acquires images of the retina while switching between the OCT mode and the LSLO mode.

In another aspect, there is an optical apparatus that includes a housing and a system of optical components disposed in the housing capable of operating in a line scanning laser ophthalmoscope (LSLO) mode and an optical coherence tomography (OCT) mode. The system of optical components includes a lens for converting between the LSLO mode and the OCT mode. The lens is movable between a first lens position and a second lens position. In the first lens position, the lens receives a beam of light from a source and provides a line of light for scanning an object in the LSLO mode. In the second lens position, the lens removed from a path of the beam of light so that the source provides the beam of light for scanning the object in the OCT mode. The optical apparatus also includes a mirror for converting between the LSLO mode and the OCT mode. The mirror is movable between a first mirror position and a second mirror position. In the first position, the mirror is removed from a path of light returning from the object. In the second position, the mirror receives the light returning from the object.

In other examples, any of the aspects above, or any apparatus or method described herein, can include one or more of the following features.

In some embodiments, the first optic includes a beam separator having an aperture that, in the LSLO mode, redirects the second light returning from the eye to the detection system. In some embodiments, the optical system can include a dichroic beamsplitter. In some embodiments, the first optic is a dichroic beam splitter. The dichroic beam splitter can be disposed in the aperture. In the OCT mode, the dichroic beam splitter disposed in the aperature uses the first surface of the dichroic beam splitter to scan the first beam of light along the retina of the eye in the first dimension and uses the first surface to descan the first light returning from the eye in the first dimension to the detection system. In the LSLO mode the second beam of light to the retina of the eye passes through the second surface of the dichroic beam splitter.

In some embodiments, the system of optical components also includes a second optic that, in the OCT mode, scans the first beam of light along the retina in a second dimension and descans the first light returning from the eye in the second dimension. The second optic can direct the first light returning from the eye to the first surface of the first optic and to the detection system. In the LSLO mode, the second optic can scan the second beam of light, in a line focus configuration, along the retina in the second dimension, and descan the second light returning from the eye in the second dimension. The second optic can direct the light returning from the eye to the first surface of the first optic and to the detection system. In some embodiments, the second optic includes a scanning mirror.

In some embodiments, the system of optical components also includes a third optic. In the OCT mode, the third optic can use a first surface of the third optic to direct the first beam of light to the first optic. The third optic can also use the first surface of the first optic to redirect the first light returning from the eye scanned. In some embodiments, the third optic uses a second surface of the third optic to redirect the first light, dispersed by a grating, to the detection system. In the LSLO mode, the third optic can pass the second light returning from the eye to the detection system. The third optic can include a dichroic beam splitter.

In some embodiments, the housing is adapted to be handheld. The first source and the second source can be the same source of light. In some embodiments, the imaging apparatus includes a controller, associated with the detection system, that switches the apparatus between the OCT and the LSLO mode. The controller associated with the detection system can also interleave the acquisition of the OCT image of the eye and the LSLO image of the eye by the detection system. In some embodiments, the OCT mode includes a spectral domain OCT mode.

In some embodiments, the system of optical components can include a scanner. In the LSLO mode, the scanner can scan through at least one lens, a first portion of the object with the line of light in a direction perpendicular to the line. The scanner can also descan light returning from the object in the LSLO line configuration. In the OCT mode, the scanner can scan a second portion of the object with the beam of light and redirect light returning from the object.

In some embodiments, the system of optical components includes a grating spectrograph, used only in the OCT mode, to disperse light returning from the object into an OCT line configuration.

The apparatus can have a first and second source of light that generates a first and second light beam. The first and second light beam can be used for the LSLO mode and the OCT mode, respectively. In some embodiments, the detection system includes a one-dimensional detector. In the OCT mode, the one dimensional detector can receive the first light returning from the eye in the first dimension and provide a first electrical signal responsive to the first light at each of a plurality of locations along the one-dimensional detector. The first electrical signal can be combined with a reference signal from a reference arm. In some embodiments, the first electrical signal and the reference signal is associated with an OCT image of the eye. In the LSLO mode, the one dimensional detector can receive a second light returning from the eye and provide a second electrical signal responsive to the second light at each of a plurality of locations along the one-dimensional detector. In some embodiments, the second electrical signal is indicative of a LSLO image of the eye.

In some embodiments, the system of optical components includes a source of the beam of light used in the LSLO mode and the OCT mode. The detection system can include a one-dimensional detector. In the LSLO mode, the detector can receive light descanned from the object and provide an electrical signal responsive to the light descanned at each of a plurality of locations along a LSLO line configuration. In some embodiments, the electrical signal is indicative of a LSLO image of the object. In the OCT mode, the detector can receive light redirected by the mirror and provide an electrical signal responsive to the light redirected at each of a plurality of locations along an OCT line configuration. The electrical signal can be combined with a reference signal from a reference arm. In some embodiments, the electrical signal and the reference signal is associated with an OCT image of the object.

In some embodiments, the apparatus includes a controller, associated with the detection system, that switches the apparatus between the OCT mode and the LSLO mode. The controller, associated with the detection system, can interleave acquisition of the OCT image of the eye and the LSLO image of the eye by the detection system. In some embodiments, the controller can interleave a first series of images of the retina acquired in the OCT mode and a second series of images of the retina acquired in the LSLO mode.

Other aspects and advantages of the invention can become apparent from the following drawings and description, all of which illustrate the principles of the invention, by way of example only.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

DETAILED DESCRIPTION OF THE INVENTION

Figure 1:
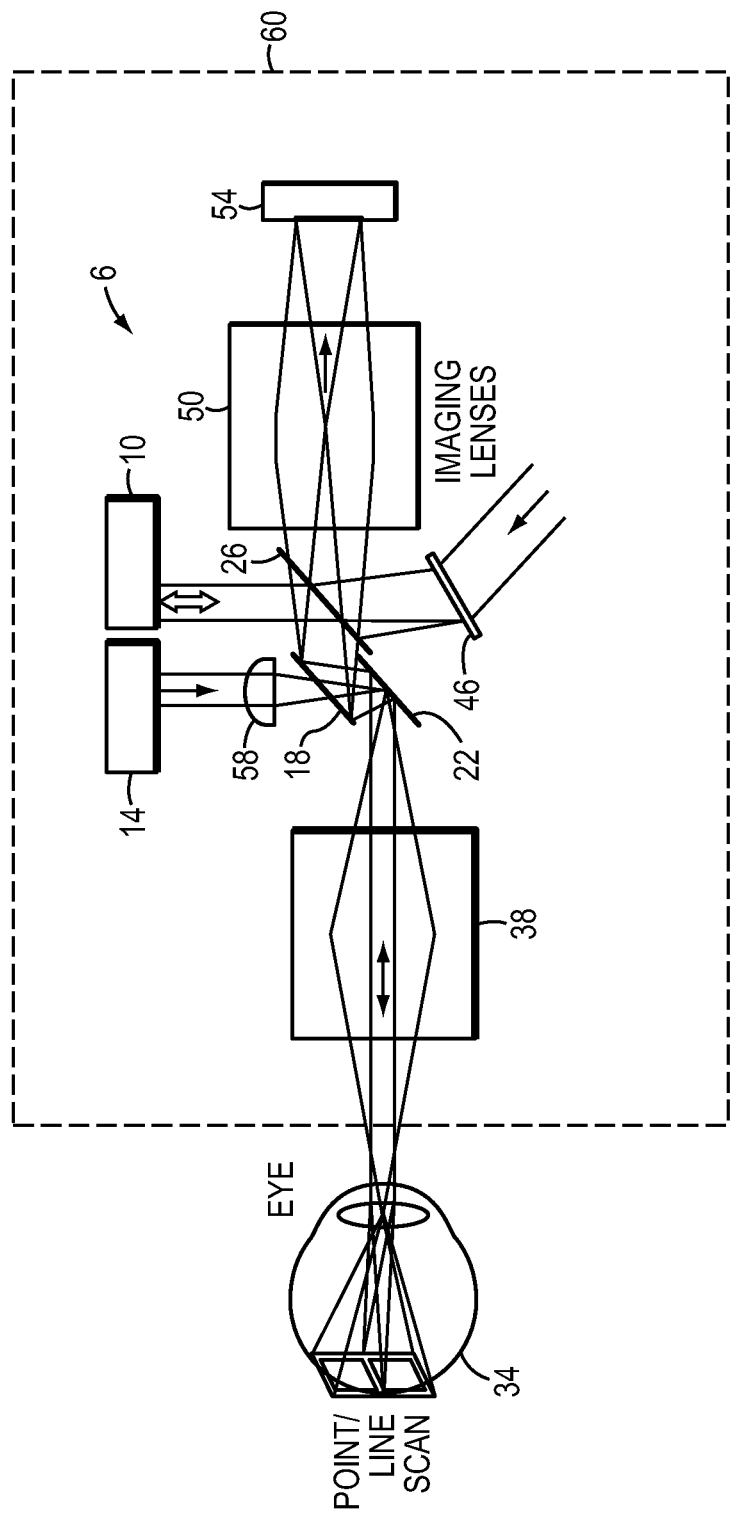
FIG. 1 is a schematic drawing of a hybrid OCT/LSLO retinal imaging system.

FIG. 1 shows an embodiment of an imaging apparatus 6 that can provide line scanning laser ophthalmoscope (LSLO) images and Optical Coherence Tomography (OCT) image. The imaging apparatus 6 can be converted between a LSLO mode and a OCT mode without the use of moving parts. Instead, a system of optical elements are implemented to combine the beam paths of the OCT and the LSLO and to scan an eye 34. A first source 10 provides a first beam of light for the OCT mode and a second source 14 provides a second beam of light for the LSLO mode. The imaging system 6 can operate in the LSLO and the OCT mode using optical elements 18, 22, and 26.

When the imaging apparatus 6 is operating in the OCT mode, the beam of light from the OCT light source 10 travels to a first surface of the optical element 26, which directs the light to a first surface of optical element 18. The line can be redirected to optical element 22, which scans the beam of light along the retina of the eye 34. In some embodiments, the light travels through a system of scanning lenses 38, which adjusts the focus of the light from the OCT source 10. The light returning from the eye 34 can be descanned by the optical element 22 and directed to the first surface of the optical element 18. The first surface of optical element 26 directs the light to a waveguide that delivers the light to a detector arm. The light is dispersed by a grating 46, and the dispersed light is redirected by the second surface of the optical element 26 to an imaging lens 50 that focus the light on a detection system 54.

When the imaging apparatus 6 is operating in the LSLO mode, a cylindrical lens 58 can be used to fan out the beam of light from the LSLO source 14 into a line on the retina of the eye 34. The line of light from the cylindrical lens 58 passes through a second surface of the optical element 18. Optical element 22 scans the beam of light on the retina of the eye 34.

Lenses 38 can focus the light on the retina of the eye 34. The light returning form the eye 34 can be descanned by the optical element 22 and redirected by the first surface of optical element 18. In the LSLO mode, the light passes through the optical element 26, and a system of imaging lenses 50 focuses the light on the detection device 54.

In some embodiments, a single source can be split to form the OCT source 10 and the LSLO source 14. The single source can be switched between an LSLO mode and an OCT mode to deliver light as the LSLO source 14 or the OCT source 10, respectively. In some embodiments, the OCT source 10 and the LSLO source 14 are two distinct sources.

A single broadband source can be split between two input fibers, or with dual super-luminescent diode (SLD) sources 10 and 14, which can be modulated. A single broadband source can also be switched between two input fibers, or with dual SLD sources 10 and 14 which can be modulated. A broadband superluminescent diode can reduce speckle noise in an SLO image. Wavelength separation can be achieved by modulating the dual-input fiber-coupled sources electronically, either as dual-SLD sources directly, or by separate fiber-optic switching or modulation of sub-bands of a single source. This approach is still compatible with single source operation, but wavelength or polarization separation can be employed, along with source-switching or modulation.

The OCT source 10 can be a near-infrared source, such as a 830-nm laser diode, an 830-nm SLD, or an 800-nm SLD with 30-nm bandwidth available from Exalos Inc. The LSLO source 14 can be a substantially point source of light, such as an infrared laser or a super-luminescent diode. For example the LSLO source 14 can be 905-nm SLD or a 920 nm SLD. In one embodiment, the OCT source 10 is a broadband super-luminescent diode (SLD-37MP, Superlum-Russia) with 830 nm central wavelength and approximately 50 nm bandwidth, and the LSLO source 14 is a 920 nm SLD (QSDM-920-2, Q-Photonics) with about 35 nm FWHM and 2 mW output power. In some embodiments, the OCT source 10 is a SLD centered at 830 nm with a spectral bandwidth of about 60 nm that achieves approximately 4 µm depth resolution in the eye.

In some embodiments, optical element 22 is a scanning mirror. In certain embodiments, optical element 22 is a dichroic beam splitter. Optical element 22 can scan and de-scan OCT light and LSLO light on or along the eye 34. In the OCT mode, optical element 22 scans one dimension of the raster scan. In the LSLO mode, optical element 22 scans a line of light along the eye 34. In some embodiments, optical element 18 is a scanning mirror. In certain embodiments, optical element 18 is a dichroic beam splitter. Optical element 18 can scan and descan OCT light on or along the eye 34. In the OCT mode, optical element 18 scans the second dimension of the retina scan. In the LSLO mode, optical element 18 can be stationary. Optical element 18 reflects LSLO light to optical element 26.

Optical element 18 can be a beam separator with an aperture. A dichroic beam splitter can be disposed in the aperture. In the LSLO mode, the dichroic beam splitter in the aperture passes the beam of light from the LSLO source through a second surface of the dichroic beam splitter to the retina of the eye. When operating in the LSLO mode, optical element 18 can also be a beam separator that separates light directed to the eye from light returning from the eye and can redirect the light returning from the eye to the detection system. In the OCT mode, the dichroic beam splitter, which can be disposed in the aperture of optical element 18 can scan, using the first surface, the beam of light along the retina of the eye in the first dimension and descan, using the first surface, the light returning from the eye in the first dimension to the detection system.

In a preferred embodiment, optical element 18 is used for scanning in the OCT mode, but is not used for scanning in the LSLO mode.

In some embodiments, optical element 26 is a dichroic beam splitter that reflects OCT light in the OCT mode. Optical element 26 can also be a dichroic beam splitter that passes LSLO light in the LSLO mode.

In some embodiments, the grating 46 is a transmission grating. The grating 46 can be a holographic diffraction grating (e.g., a grating available from Wasatch Photonics with 1200 lines per mm). The detection device 54 can be a linear array detector. For example, the detection device can be a CCD array or a CMOS detector.

The imaging apparatus 6 can run in three modes: LSLO mode only, OCT mode only, and frame-interleaved LSLO/OCT mode. The detection device 54 can record a sequence of OCT images and LSLO images. In some embodiments, no moving parts are required to change imaging modes: a simple software switch controls the hardware configuration for each imaging mode "on the fly". When switched, the desired source can be turned on (and the other off) and the camera gain is changed if necessary, as are the transverse scan parameters of the data acquisition card. Thus, the LSLO and OCT systems can be integrated in a unique manner with a common detection path that conserves sub-system capabilities and minimizes size, cost, and complexity.

In some embodiments, an OCT image is recorded first. In other embodiments, a LSLO image is recorded first. In some embodiments, the detection device in the OCT mode receives light returning from the eye in the first dimension and provides a first electrical responsive to the first light at a plurality of locations along a one dimensional detector. The electrical signal can be combined with a reference signal from a reference arm where the first electrical signal and the reference signal is associated with an OCT image of the eye. In some embodiments, the detection device in the LSLO mode receives light returning from the eye and provides a second electrical signal responsive to the second light at a plurality of locations along the one-dimensional detector. The second electrical signal can be indicative of an LSLO image of the eye.

The CCD array can be a line scan camera (e.g., Atmel AVIIVA M2 CL 1014 or an array available from Basler Vision Technologies). The CCD array can have 1024 detector pixels with a 14 µm pitch and can operate at a maximum 60 MHz data rate. The output of the camera can be connected to a camera link board (NI PCI-1429). The sampled data can be transferred continuously to computer memory. A λ to ω (or k) interpolation can be performed. A discrete Fourier transform can be performed on each set of 1024 data points acquired by the CCD array to produce an axial depth profile of the sample (A-line).

The CMOS detector can be a linear array detector. In one embodiment, the detector is a 512 pixel (21 µm pitch) linear CMOS detector with active reset technology with high sensitivity and low read noise (e.g., available from Fairchild Imaging). In one embodiment, the detector is a 2048 pixel (7 µm pitch) CMOS detector with line rates to 40 kHz.

In some embodiments, a controller is associated with the detection system that switches the imaging apparatus between the OCT mode and the LSLO mode. In some embodiments, imaging modes can be switched fast enough to interleave LSLO and SDOCT images. The images can be interleaved at any desired rate and in any desired sequence or combination, using software control with no mechanical mode-switching transients. The device can rapidly toggle back and forth between LSLO mode and SDOCT mode frame by frame, coordinated by the scanning and signal processing electronics, e.g., to give the appearance that both operate at once: SDOCT on the forward scan, and LSLO on the flyback of the scan.

Components of the imaging apparatus 6 can be contained within a housing 60. In some embodiments, the housing 60 can be compact and hand-held. The OCT system can be a SDOCT.

Figure 2:
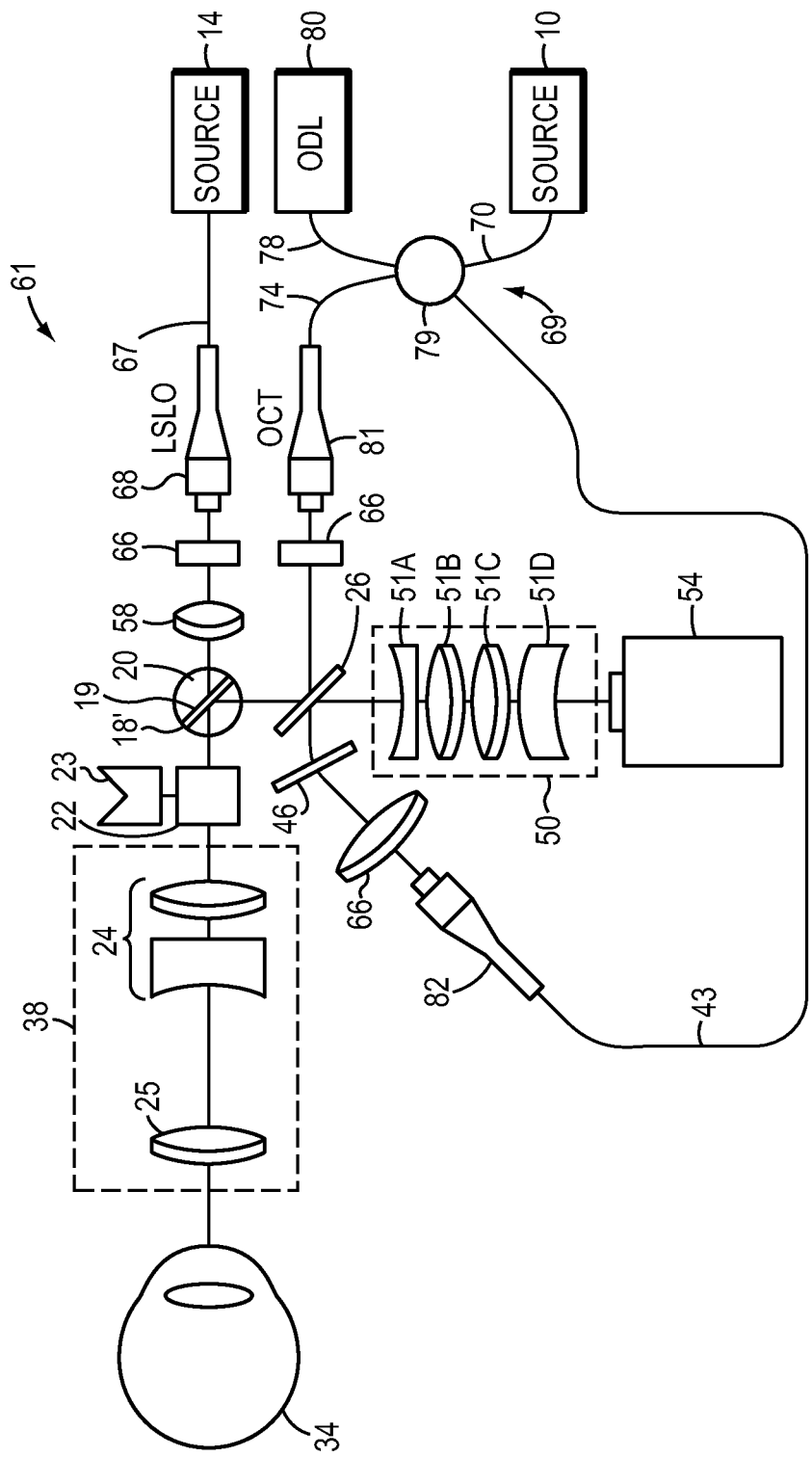
FIG. 2 is another schematic drawing of a hybrid OCT/LSLO retinal imaging system.

FIG. 2 demonstrates another embodiment of a hybrid imaging apparatus 61 for imaging the eye 34. First optical element 18' can be a mirror 20 with a dichroic beam splitter 19 mounted in an aperture of the mirror 20. The dichroic beam splitter 19 can be mounted on an x-axis galvanometer. When the light returns from the eye, the first surface of the optical element 18' can be used to redirect the light to the detection system 54.

In the OCT mode, the first surface of the optical element 18' scans the light traveling to the eye 34 in a raster scan and redirects the light returning from the eye 34. The optical element 18' can descan the light. In the LSLO mode, light from source 14 travels through the second surface of optical element 18' to the retina of the eye. The light can travel to optical element 22 which can be driven by a galvanometer 23 that drives the optical element 22 in a direction along the y-axis. The scanning lenses 38 can include a objective lenses 24 and an ophthalmoscopic lens 25.

The imaging lens 50 can be a system of imaging lenses. For example, a plurality of objectives 51A-D can gather light returning from the eye in the OCT mode or the LSLO mode and direct the light to the detection system 54.

A collimating lens 66 can be used to adjust the optical elements to maximize the quality of the image. In the LSLO mode, light from the LSLO source 14 can be directed through a waveguide 67 to a coupler 68, and from the coupler 68 to a first collimating lens 66, which directs the light to the cylindrical lens 58.

In some embodiments, an SDOCT system includes light source 10 and a fiber-optic interferometer 69. The fiber optic interferometer 69 can include a coupler 79 that receives and/or directs light to four arms: the illumination arm, the sample arm, the reference arm, and the detection arm. In some embodiments, the coupler is a 50/50 or a 80/20 fiber optic beam-splitter. Light from the light source 10 can be directed to the coupler 79 via waveguide 70. The coupler 79 can divide the light and direct a portion to the sample arm via waveguide 74 and a portion to the reference arm via waveguide 78. A fraction of the light transmitted to the sample arm can be backscattered from the sample, and passed back into the coupler 79. A fraction of the light transmitted to the reference arm can be backscattered from an optical delay line (ODL) 80, passed back into the coupler 79.

The optical delay line 80 can include a mirror placed on a translation stage and a neutral density filter that adjusts this arm's power level. The optical delay line 80 can be placed in the reference arm to adjust the length of this arm to match the length of the sample arm. The polarization of the reference beam can be adjusted with a paddle polarization controller to match the polarization of the light from the sample arm, so that polarization changes caused by bending and rotation of the optical fiber in both the sample and reference arms do not wash out the interference fringes. The coupler 79 can mix the reference beam with the light returning from the sample arm. In some embodiments, this light passes back to the input arms, being equally split between the detector arm and the illumination arm. The light is sent to the detector arm through a waveguide 43. An isolator can be placed in the illumination arm to prevent this light from going back to the light source 10. Light from waveguide 74 can be directed to a second collimating lens 66 via a coupler 81.

The SDOCT system also includes a spectrometer system. The light directed to the detector arm from waveguide 43 passes through coupler 82 and to a third collimating lens 66. The light is dispersed by a grating 46 and received by the detection device 54.

Figure 3:
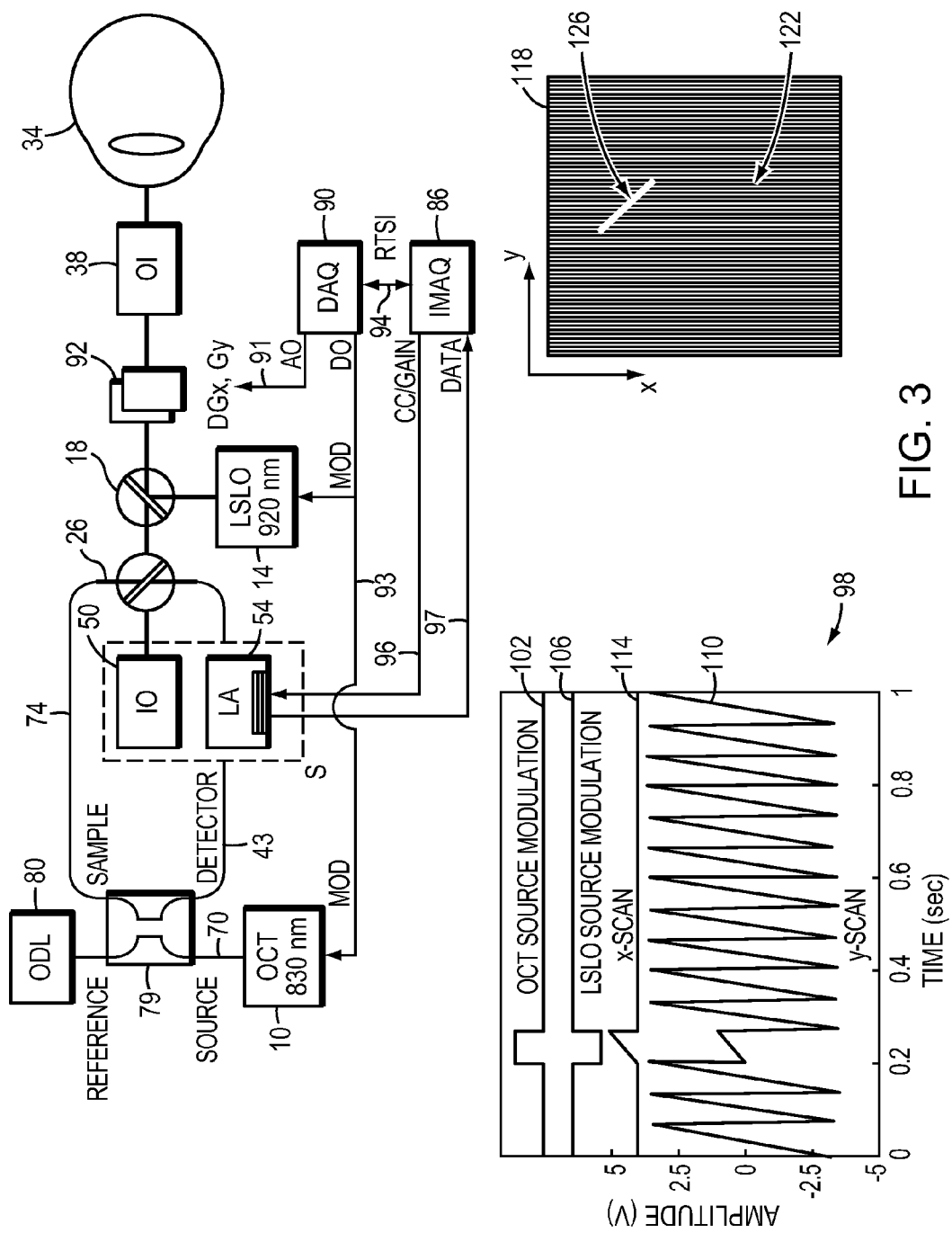
FIG. 3 is a schematic drawing of the command lines, imaging raster, and timing sequence of a hybrid OCT/LSLO retinal imaging system.

FIG. 3 shows a schematic of the command lines, imaging raster, and timing sequence according to an illustrative embodiment of the imaging apparatus. In some embodiments, an image acquisition board (IMAQ) 86 e.g., a cameralink framegrabber is used for data collection while a data acquisition (DAQ) board 90 is used for instrument timing. The analog output 91 can be used to control galvometer(s) 92 that control optical element 22. A first digital line 93 can be to turn "on" and "off" any of the light sources for the OCT light source 10 or the LSLO light source 14. A second digital line, the real time system integration line (RTSI) 94 can be used to control the camera gain. The IMAQ 86 provides control signals 96 and receives data 97 from the detection device 54. The control signal 96 can be a gain control for the detection device 54.

In certain embodiments, the detection device 54 is operated in a high gain mode when the imaging apparatus is operating in LSLO mode and a low gain mode when the imaging apparatus is operating in OCT mode. The OCT is an interferometric measurement, which functions with the least noise when the amplifying reference beam power is set to the maximum value that will not saturate the camera at its lowest gain (sensitivity) setting. This can give the maximum possible fringe amplitude (OCT signal) relative to camera noise and digitization levels. The LSLO is a direct imaging method that can rely on high camera sensitivity to image the weak fundus reflectance. In some embodiments, the camera gain setting for the LSLO is the maximum value available that does not saturate, in order to maintain the best digital resolution over the dynamic range. In some embodiments, the optimal camera gains for the OCT and the LSLO are different and require the gain to be toggled electronically between two values in switching between imaging modes so that the performance is optimized for each mode. Alternatively, the LSLO input beam power can be set higher to account for the required sensitivity difference (e.g., up to a limit set by ANSI eye safety standards). The gain of cameras (e.g., the ATMEL line scan camera) can be changed with serial digital commands, or more directly with digital control signals synchronized to the frame rates.

The timing diagram 98 shows the combined LSLO/OCT mode when OCT data can be acquired. A comparison of the OCT source modulation 102 and the LSLO source modulation 106 shows that the OCT light source is turned "on" while the LSLO source is turned "off". In some embodiments, the amplitude of the y-galvanometer 110 versus the amplitude of the x-galvanometer 114 over time is such that the y-galvanometer moves to the selected y-coordinate, and the x-galvanometer scans the OCT beam over a smaller distance. In diagram 118, the distance covered by the LSLO raster scan 122 is compared to the distance covered by the OCT scan 126.

Figure 4:
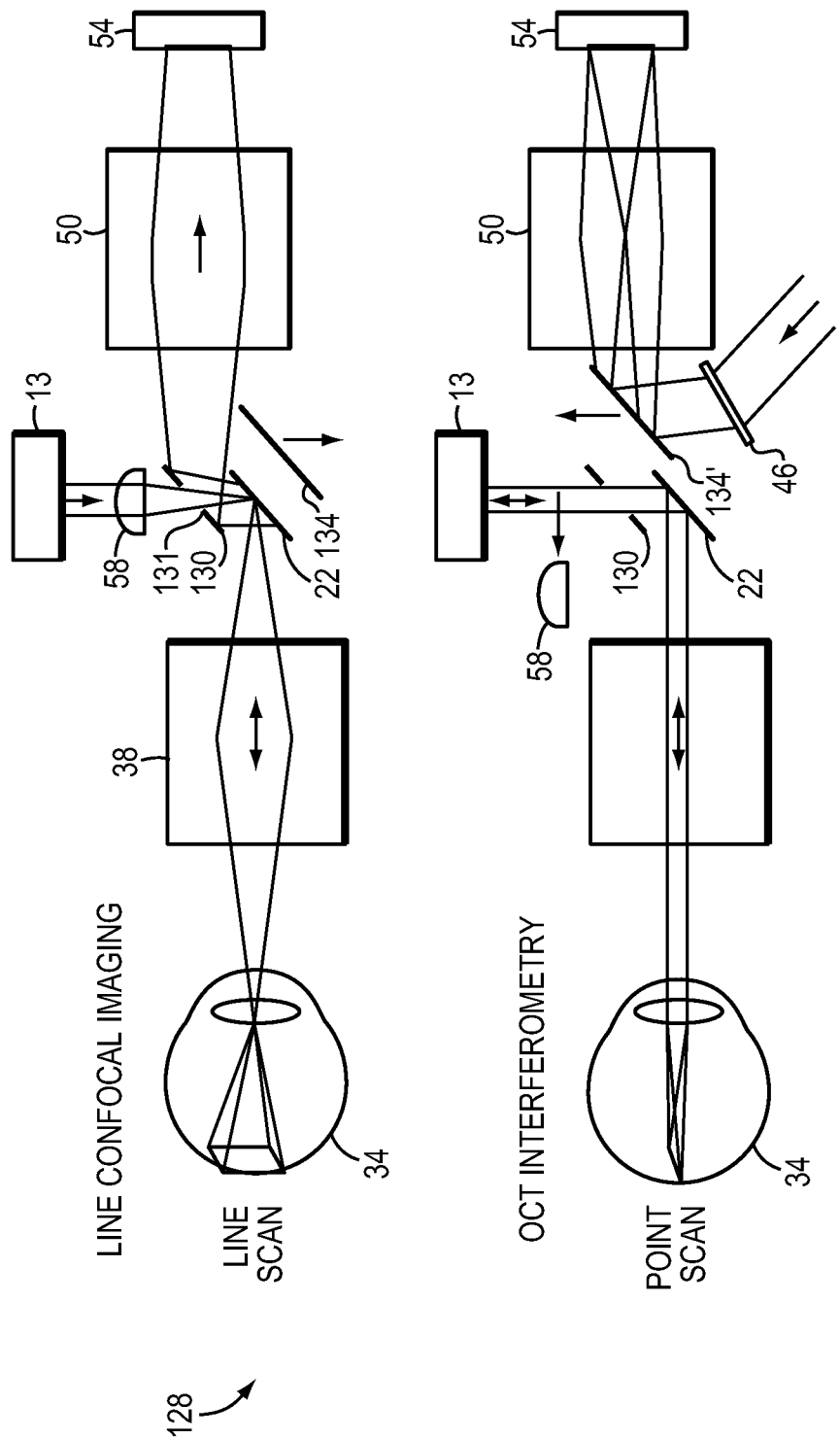
FIG. 4 is a schematic drawing of an apparatus that uses moving parts to convert between the OCT mode and the LSLO mode, according to an illustrative embodiment.

FIG. 4 demonstrates another embodiment of the imaging apparatus 128 using moveable parts to operate the apparatus in the LSLO and OCT modes. FIG. 4 shows the LSLO and OCT beams paths separated for clarity. The moveable parts can include a removable cylindrical lens 58 and a flip mirror 134. The lens moves between a first lens position 58 and a second lens position 58' to convert between the LSLO mode and the OCT mode. The mirror can move between a first mirror position 134 and a second mirror position 134' to convert between the LSLO mode and the OCT mode.

A single source 13 can be used to supply light in both the LSLO and OCT mode. In some embodiments, optical element 130 allows both the OCT and LSLO beam to travel through an aperture 131. In the OCT mode, the optic 130 can permit the returning light to pass through the same path (e.g., through the aperture 131), but in the LSLO mode, directs the beam to the detection system 54. For example, a surface above, below, or surrounding the aperture can 131 can reflect the light in the LSLO mode. The optical element 130 can be a mirror. The same detection system 54 can also be used for both the LSLO and OCT modes.

In the LSLO mode, in the first lens position, the lens 58 receives a beam of light from the source 13 and provides a line of light for scanning an object. The beam travels through optical element 130 to optical element 22, which scans, through a scanning lens(es) 38 the eye 34. The light returning from the eye can be descanned by optical element 22 and directed to the detection device 54 by the optical element 130. In the LSLO mode, the flip mirror 134 is flipped out.

In the OCT mode, in the second lens position, the lens 58' is removed from the path of the beam of light so that the source 13 provides the beam of light for scanning the object. The beam of light can travel through optical element 130 to optical element 22, which scans the light in a raster pattern over a portion of the eye 34. The light returning from the eye is directed by optical element 22 to optical element 130. The light can pass back through the pupil, which functions as an interferometer. The light travels through the sample arm to the coupler 79, which mixes the beam with the light from a reference arm as shown in FIGS. 2-3. A part of the mixed beam from the coupler 79 is sent to the detector arm where the beam is dispersed by the grating 46. In the OCT mode, the flip mirror 134' directs the light dispersed by the grating 46 to the detection device 54.

Without the cylindrical lens 58' in the beam path and the mirror 134' flipped in, the system can operate as a high-resolution 30 fps SDOCT scanner showing cross-sectional image of the retina at selected planes. With the lens 58 in place and the mirror 134 flipped out, the SLD beam can be fanned into a focused line, and the system can be converted into a quasi-confocal LSLO en face wide-field retinal imager. In some embodiments, the actuated cylindrical lens 58 and mirror 134 permit mode switching within less than about 1 frame period. The SLD source module can be integrated into the optics package. A tether can be used connect to an external source and power module. In certain embodiments, batteries can be used.

Figure 5:
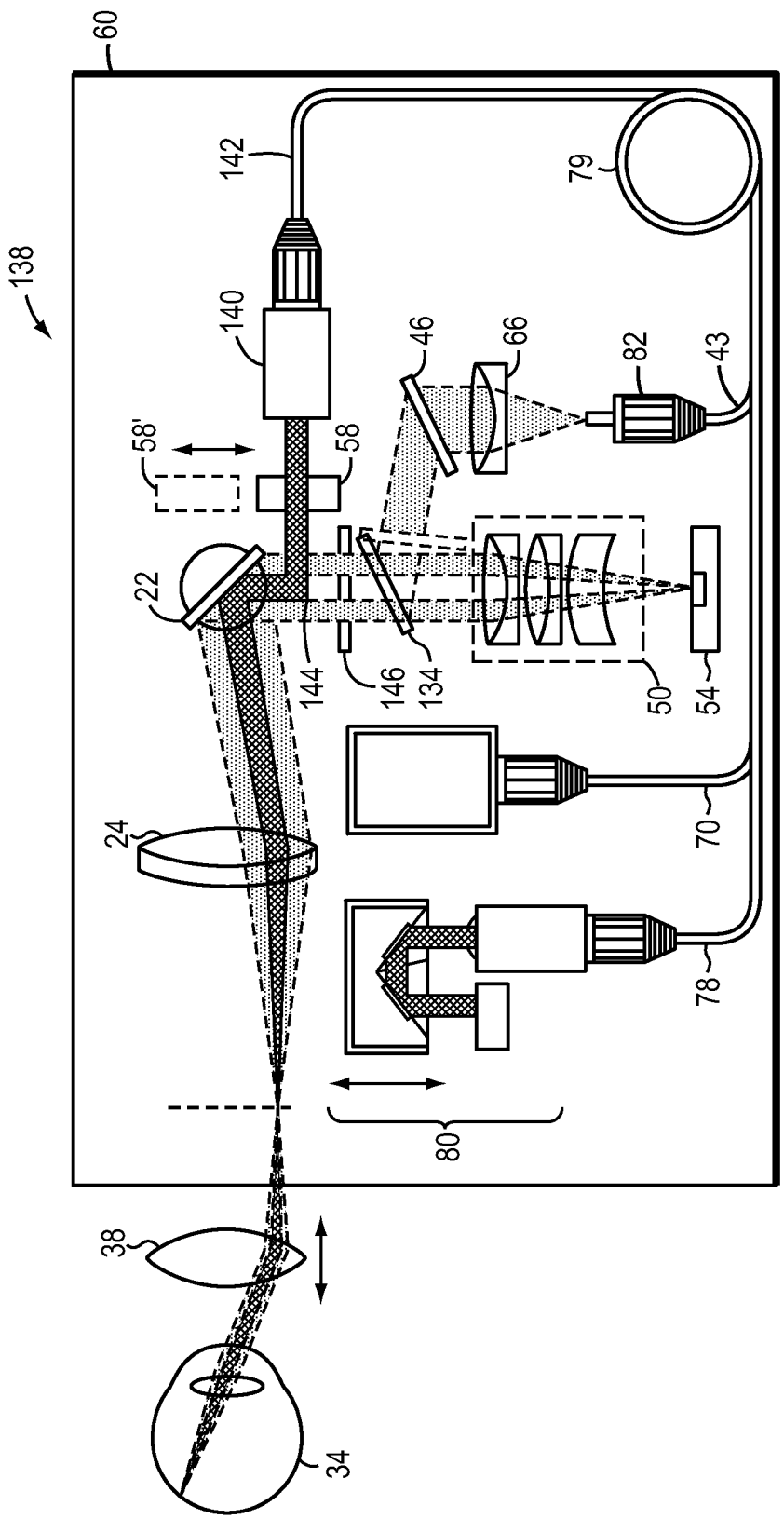
FIG. 5 is another schematic drawing of an apparatus that uses moving parts to convert between the OCT mode and the LSLO mode.

FIG. 5 shows another illustrative embodiment of an imaging apparatus 138 that includes moveable parts to convert between an OCT mode and an LSLO mode. The same light source 13 and detection system 54 can be used for both the OCT mode and LSLO mode. Light source 13 directs light to coupler 140 via waveguide 142 in the sample arm.

In the LSLO mode, the coupler 140 directs light to the lens 58, which directs light to optical element 144. Optical element 144 directs light to optical element 22, which can scan the beam of radiation on the eye 34, Light returning from the eye 34 passes by and/or around optical element 144 and through pupil stop 146. Flip mirror 134 is removed from the optical path.

In the OCT mode, lens 58 is in position 58' (e.g., it is removed from the beam path). The light is directed by optical element 144 to optical element 22. Light returning from the eye 34 is reflected by optical element 144 back into waveguide 142. The light emerges from waveguide 43 and is dispersed by grating 46 before it is reflected by mirror 134 to the detection device 54.

Optical element 144 can be a mirror or prism. Optical element 146 can be a pupil stop and/or a pupil aperture. The subdivision of the pupil aperture can allow the efficient integration of the subsystems and elimination of unwanted reflections (e.g., corneal reflections). In some embodiments, the scanning optical delay in the OCT reference arm 78 compensates for pupil position, eye length and/or focus. With a flip mirror 134, both imaging systems can use the same linear array detector 54.

Figure 6:
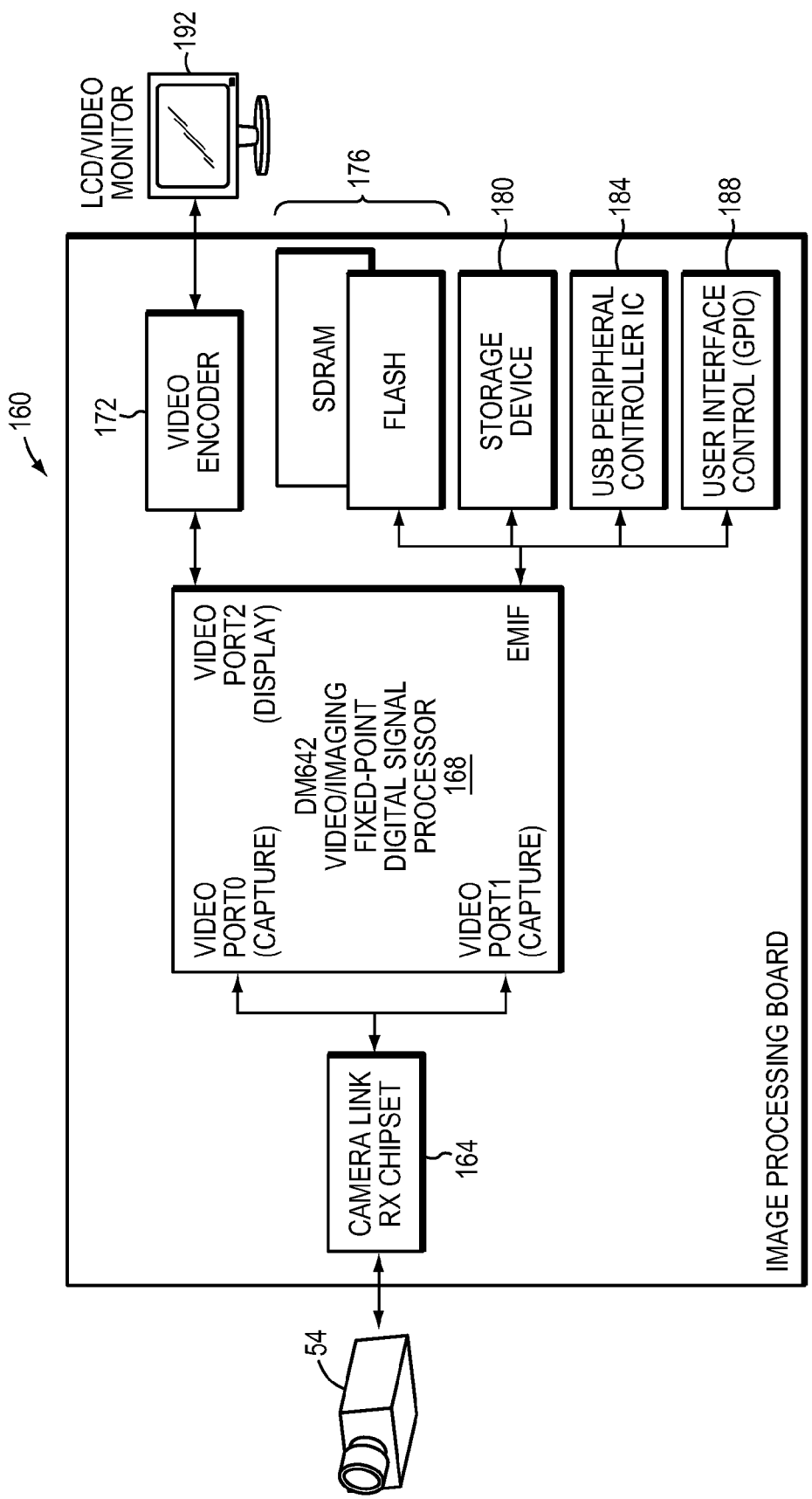
FIG. 6 is a block diagram of an exemplary chipset for use in a hybrid OCT/LSLO retinal imaging system.

The linear image sensor, the spectrometer, the image acquisition, and the processing electronics can reduce the cost and complexity of a hybrid imaging system. FIG. 6 shows a block diagram of an exemplary chipset 160. A stand-alone FPGA/ DSP electronics platform (e.g., not tethered to a PC) can be used for real-time LSLO and OCT signal processing and integrated display. The chipset 160 can include a camera link 164, a signal processor 168, a video encoder 172, memory 176, a storage module 180, a USB controller 184, and a user interface 188.

The camera link 164 can be coupled to the detection device 54. The video encoder can be coupled to a display device 192. The memory 176 can be SDRAM, flash memory, and/or any other suitable memory. The storage device 180 can be a compact flash, smart media, SD, or MMC. The USB controller can include a USB interface.

The user interface 188 and display device 192 can display an LSLO image and a OCT image separately or simultaneously (depending on the imaging mode), and the OCT scan can be positioned anywhere in the LSLO raster. Other controls for OCT processing, display, and saving or streaming to disk are in a tab box in the display. The raw spectrum and processed profile can be shown, and the integrated fixation target can be displayed.

In some embodiments, an FPGA camera board with integrated SVGA LCD display driver for a CMOS line array can obviate the need for a PC and frame grabber tethered to the optical scanner head. In certain embodiments, real time FFTs on SDOCT line scan data and display can be performed using the signal processor chipset 168 (e.g., a DM642 fixed-point DSP or an FPGA). The detection device 54 can be connected to the signal processor via camera-link RX Chipset 164. A suitable signal processing approach or algorithm with associated hardware and software for SDOCT signal processing algorithm can include such an interpolation to k-space process. Dispersion compensation can be incorporated in the software for real time operation.

LSLO-guided 2D SDOCT sections and localized 3D (micro-scan) SDOCT imaging modalities can be used as part of the imaging mode control software. In some embodiments, by overlaying a fiducial line or box over the live LSLO image display, which represents the length, position and orientation of the SDOCT scan(s) to be captured in the next frame(s), the operator can precisely scan selected retinal features at the desired resolution. 3D structure can be visualized by sweeping the line scan manually push broom-style.

In some embodiments, local 3D images can be captured and displayed (e.g., a micro-scan option). In some embodiments, a resonant scanner is used to perform a low speed, small amplitude scan. The resonant scanner can be added to the SDOCT beam path, orthogonal to the main galvo scanner. Instead of performing a single long linear scan of 5 mm or more when a very small feature such as a laser lesion is of interest, the system can be commanded to perform many smaller scans in a raster pattern: perhaps twenty or more 0.5 mm B-scans with 10 micron pixellation in x (50 A-scans) and 25 μm pixels in y (20 B-scans). Thus, the entire raster can include 1000 A-scans, which can be displayed as one composite B-scan. 500×500 micron×2 mm high-resolution SDOCT volume images can be provided. Such an approach can be used for elucidating columnar laser damage or localized pathology. A fiducial box can be overlaid in the live LSLO image for this selectable mode, with real time display of the successive SDOCT stripe images.

Estimates of 3D micro-scan speed can be obtained from digital signal processor benchmark data. The 1024 point FFT benchmark for the DM642 is less than about 16 μs per FFT. The CCD array or CMOS detector can have line rates in excess of 25 Klps. At this line rate, the resulting frame rate for 1000 A-scans of the Micro-scan raster (50×20) is about 25 fps (0.04 sec/frame). Real time 3D micro-scans with rapid intuitive display of 3D data can be performed. In some embodiments, a FPGA signal processor is utilized to provide a scan showing local 3D structures.

While the invention has been particularly shown and described with reference to specific illustrative embodiments, it should be understood that various changes in form and detail may be made without departing from the spirit and scope of the invention.

What is claimed:

1. A method of imaging a retina of an eye, comprising:
   combining an optical path of an optical coherence tomography (OCT) imager and an optical path of a line scanning laser ophthalmoscope (LSLO) imager using a system of optics, the system of optics is disposed in a housing capable of operating in a LSLO mode and an OCT mode, the system of optics including:
   a first source to provide a first beam of light for the OCT imager,
   a second source to provide a second beam of light for the LSLO imager, and
   a first optic that:
      in the OCT mode, (i) scans, using a first surface of the first optic, the first beam of light along a retina of an eye in a first dimension, and (ii) descans, using the first surface, a first light returning from the eye in the first dimension to the single detector, and
      in the LSLO mode, (i) passes, through a second surface of the first optic, the second beam of light to the retina of the eye;
   switching between the OCT mode and the LSLO mode;
   using a single detector to image in both the OCT mode and the LSLO mode depending on which mode is selected; and
   acquiring images in both the OCT mode and the LSLO mode depending upon which mode is selected.

2. The method of claim 1 wherein the single detector comprises a one-dimensional detector that:
   in the OCT mode, receives the first light returning from the eye in the first dimension and provides a first electrical signal responsive to the first light at each of a plurality of locations along the one-dimensional detector, the first electrical signal combined with a reference signal from a reference arm, the first electrical signal and the reference signal associated with an OCT image of the eye; and
   in the LSLO mode, receives a second light returning from the eye and provides a second electrical signal responsive to the second light at each of a plurality of locations along the one-dimensional detector, the second electrical signal indicative of a LSLO image of the eye.

3. The method of claim 2 wherein the system of optics further comprises:
   a second optic that:
      in the OCT mode, (i) scans the first beam of light along the retina in a second dimension, and (ii) descans the first light returning from the eye in the second dimension, the first light returning from the eye directed to the first surface of the first optic and to the single detector; and
      in the LSLO mode, (i) scans the second beam of light, in a line focus configuration, along the retina in the second dimension, and (ii) descans the second light returning from the eye in the second dimension, the light returning from the eye directed to the first surface of the first optic and to the single detector.

4. The method of claim 2 wherein the system of optics further comprises:
   a second optic that:
      in the OCT mode, (i) directs, using a first surface of the second optic, the first beam of light to the first optic, (ii) redirects, using the first surface of the first optic, the first light returning from the eye scanned, and (iii) redirects, using a second surface of the second optic, the first light, dispersed by a grating, to the single detector; and
      in the LSLO mode, passes the second light returning from the eye to the single detector.

5. The method of claim 1 wherein the first optic comprises:
   a beam separator, having an aperture, that, in the LSLO mode, redirects the second light returning from the eye to the single detector; and
   a dichroic beam splitter, disposed in the aperture, that:
      in the OCT mode, (i) scans, using the first surface of the dichroic beam splitter, the first beam of light along the retina of the eye in the first dimension, and (ii) descans, using the first surface, the first light returning from the eye in the first dimension to the single detector; and
      in the LSLO mode, (i) passes, through the second surface of the dichroic beam splitter, the second beam of light to the retina of the eye.

6. The method of claim 3 wherein the second optic comprises a scanning mirror.

7. The method of claim 4 wherein the third optic comprises a dichroic beam splitter.

8. The method of claim 1 wherein the first source and the second source are the same source of light.

9. A method of imaging a retina of an eye, comprising:
   combining an optical path of an optical coherence tomography (OCT) imager and an optical path of a line scanning laser ophthalmoscope (LSLO) imager using a system of optics, the system of optics is disposed in a housing capable of operating in a LSLO mode and an OCT mode, the system of optics including:
   a first optic that:
      in the OCT mode, (i) redirects, using a first surface of the optic, a beam of light from a first source to an object to be scanned, (ii) redirects, using the first surface, light returning from the object scanned, and (iii) redirects, using a second surface of the optic, light dispersed by a grating to the single detector, and
      in the LSLO mode, passes light returning from the object scanned to the single detector;
   combining an optical path of an optical coherence tomography (OCT) imager and an optical path of a line scanning laser ophthalmoscope (LSLO) imager using a system of optics;

switching between an OCT mode and an LSLO mode;
using a single detector to image in both the OCT mode and the LSLO mode depending on which mode is selected; and
acquiring images in both the OCT mode and the LSLO mode depending upon which mode is selected.

10. The method of claim 9 wherein the single detector comprises a one-dimensional detector that:
in the LSLO mode, receives light descanned from the object and provides an electrical signal responsive to the light descanned at each of a plurality of locations along a LSLO line configuration, the electrical signal indicative of a LSLO image of the object; and
in the OCT mode, receives light redirected by the grating and provides an electrical signal responsive to the light redirected at each of a plurality of locations along an OCT line configuration, the electrical signal combined with a reference signal from a reference arm, the electrical signal and the reference signal associated with an OCT image of the object.

11. The method of claim 9 wherein the first optic comprises dichroic beam splitter.

12. A method of imaging a retina of an eye, comprising:
wherein combining an optical path of an optical coherence tomography OCT) imager and an optical path of a line scanning laser ophthalmoscope (LSLO) imager using a system of optics, the system of optics is disposed in a housing capable of operating in a LSLO mode and an OCT mode, the system of optics including:
a first source of a beam of light suitable for use in the LSLO imager,
a second source of a beam of light suitable for use in the OCT imager,
a lens receiving the beam of light from the first source and providing a line of light for use in the LSLO imager,
an optic that:
in the OCT mode, (i) redirects, using a first surface of the optic, a beam of light from the second source to an object to be scanned, (ii) redirects, using the first surface, light returning from the object scanned, and (iii) redirects, using a second surface of the optic, light dispersed into an OCT line configuration by a grating to the single detector, and
in the LSLO mode, passes light returning from the object scanned to the single detector, and
a scanner that:
in the LSLO mode, scans, through at least one lens, a first portion of an object with the line of light in a direction perpendicular to the line, and descans light returning from the object in a LSLO line configuration, and
in the OCT mode, scans a second portion of the object with the beam of light, and redirects light returning from the object,
wherein the single detector comprises a one-dimensional detector that:
in the LSLO mode, receives the light descanned from the object and provides an electrical signal responsive to the light descanned at each of a plurality of locations along the LSLO line configuration, the electrical signal indicative of a LSLO image of the object, and
in the OCT mode, receives the light redirected from the grating and provides an electrical signal responsive to the light redirected at each of a plurality of locations along the OCT line configuration, the electrical signal combined with a reference signal from a reference arm, the electrical signal and the reference signal associated with an OCT image of the object
switching between the OCT mode and the LSLO mode;
using a single detector to image in both the OCT mode and the LSLO mode depending on which mode is selected; and
acquiring images in both the OCT mode and the LSLO mode depending upon which mode is selected.

13. The method of claim 12 wherein the optic comprises a dichroic beam splitter.

14. The method of claim 12 wherein the OCT imager comprises a spectral domain OCT imager.

15. A method of imaging a retina of an eye, comprising:
combining an optical path of an optical coherence tomography (OCT) imager and an optical path of a line scanning laser ophthalmoscope LSLO imager using a system of optics, the system of optics is disposed in a housing capable of operating in a LSLO mode and an OCT mode, the system of optics including:
a lens for converting between the LSLO mode and the OCT mode, the lens movable between a first lens position and a second lens position:
in the first lens position, the lens receives a beam of light from a source and provides a line of light for scanning an object in the LSLO mode, and
in the second lens position, the lens removed from a path of the beam of light so that the source provides the beam of light for scanning the object in the OCT mode, and
a mirror for converting between the LSLO mode and the OCT mode, the mirror movable between a first mirror position and a second mirror position:
in the first position, the mirror is removed from a path of light returning from the object, and
in the second position, the mirror receives the light returning from the object,
switching between an OCT mode and an LSLO mode;
using a single detector to image in both the OCT mode and the LSLO mode depending on which mode is selected; and
acquiring images in both the OCT mode and the LSLO mode depending upon which mode is selected.

16. The method of claim 15 wherein the system of optics further comprises a scanner that:
in the LSLO mode, scans, through at least one lens, a first portion of the object with the line of light in a direction perpendicular to the line, and descans light returning from the object in the LSLO line configuration; and
in the OCT mode, scans a second portion of the object with the beam of light, and redirects light returning from the object.

17. The method of claim 16 wherein the single detector is a one-dimensional detector that:
in the LSLO mode, receives light descanned from the object and provides an electrical signal responsive to the light descanned at each of a plurality of locations along a LSLO line configuration, the electrical signal indicative of a LSLO image of the object; and
in the OCT mode, receives light redirected by the mirror and provides an electrical signal responsive to the light redirected at each of a plurality of locations along an OCT line configuration, the electrical signal combined with a reference signal from a reference arm, the electrical signal and the reference signal associated with an OCT image of the object.

18. The method of claim 15 wherein the system of optics further comprises a single source of the beam of light used in both the LSLO mode and the OCT mode.

19. The method of claim 15 wherein the system of optics further comprises a grating spectrograph, used only in the OCT mode, dispersing light returning from the object into an OCT line configuration.

20. The method of claim 15 wherein the OCT imager comprises a spectral domain OCT imager.

* * * * *

UNITED STATES PATENT AND TRADEMARK OFFICE
CERTIFICATE OF CORRECTION

PATENT NO. : 8,770,751 B2  
APPLICATION NO. : 13/237419  
DATED : July 8, 2014  
INVENTOR(S) : R. Daniel Ferguson et al.

Page 1 of 1

It is certified that error appears in the above-identified patent and that said Letters Patent is hereby corrected as shown below:

IN THE CLAIMS:

In claim 12, column 15, line 24

Delete – "wherein"

In claim 15, column 16, line 17

Insert --( )-- before LSLO and after – "(LSLO)"

Signed and Sealed this
Thirtieth Day of December, 2014

Michelle K. Lee
*Deputy Director of the United States Patent and Trademark Office*